United States Patent
Han et al.

(10) Patent No.: US 10,246,699 B2
(45) Date of Patent: Apr. 2, 2019

(54) MICROPARTICLE SEPARATION APPARATUS ASSEMBLY COMPRISING MULTIPLE SEPARABLE PANELS

(71) Applicant: INJE UNIVERSITY INDUSTRY-ACADEMIC COOPERATION FOUNDATION, Gimhae-si, Gyongsangnam-do (KR)

(72) Inventors: Ki Ho Han, Busan (KR); Hyung Seok Cho, Busan (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 0 days.

(21) Appl. No.: 15/564,371

(22) PCT Filed: May 18, 2015

(86) PCT No.: PCT/KR2015/004938
§ 371 (c)(1),
(2) Date: Oct. 4, 2017

(87) PCT Pub. No.: WO2016/163587
PCT Pub. Date: Oct. 13, 2016

(65) Prior Publication Data
US 2018/0127736 A1  May 10, 2018

(30) Foreign Application Priority Data
Apr. 8, 2015 (KR) .................. 10-2015-0049370

(51) Int. Cl.
*C12M 1/12* (2006.01)
*C12N 13/00* (2006.01)
(Continued)

(52) U.S. Cl.
CPC ........ *C12N 13/00* (2013.01); *B01L 3/502761* (2013.01); *B03C 1/025* (2013.01);
(Continued)

(58) Field of Classification Search
CPC ......... C12N 13/00; B03C 1/025; B03C 1/288; C12M 1/12
See application file for complete search history.

(56) References Cited

U.S. PATENT DOCUMENTS 9,188,615 B2 * 11/2015 Sturmer ............ B01L 3/502792
2003/0206832 A1 * 11/2003 Thiebaud .......... B01L 3/502707
422/400

(Continued)

FOREIGN PATENT DOCUMENTS

KR        20120138684 A * 12/2012 ............. G01N 35/08

*Primary Examiner* — Terrell H Matthews
(74) *Attorney, Agent, or Firm* — Lucas & Mercanti, LLP

(57) ABSTRACT

The present invention relates to a microparticle separation apparatus assembly comprising multiple separable panels, more specifically, to a microparticle separation apparatus assembly having a novel structure, comprising: a first panel comprising a magnetic microstructure for applying magnetophoretic force to microparticles; and a second panel, which can be separated from the first panel and through which a sample comprising microparticles passes, wherein the first panel comprising the magnetic microstructure can be recycled.

13 Claims, 13 Drawing Sheets

(51) Int. Cl.
*B03C 1/28* (2006.01)
*C12M 1/42* (2006.01)
*C12Q 1/24* (2006.01)
*B03C 1/025* (2006.01)
*B01L 3/00* (2006.01)
*C12M 1/00* (2006.01)
*G01N 33/50* (2006.01)

(52) U.S. Cl.
CPC ............... *B03C 1/288* (2013.01); *C12M 1/12* (2013.01); *C12M 1/42* (2013.01); *C12M 47/02* (2013.01); *C12Q 1/24* (2013.01); *G01N 33/50* (2013.01); *B03C 2201/18* (2013.01); *B03C 2201/26* (2013.01)

(56) References Cited

U.S. PATENT DOCUMENTS

| | | | |
|---|---|---|---|
| 2011/0003303 A1* | 1/2011 | Pagano | B01L 3/502761 435/6.19 |
| 2011/0284420 A1* | 11/2011 | Sajid | G06F 1/1628 206/576 |
| 2012/0195810 A1* | 8/2012 | Cohen | B01L 3/502738 422/502 |
| 2013/0189755 A1* | 7/2013 | Han | B03C 1/0335 435/173.9 |
| 2014/0021105 A1* | 1/2014 | Lee | G01N 27/44756 209/214 |
| 2018/0126381 A1* | 5/2018 | Huff | B01L 3/502715 |

* cited by examiner

[FIG. 1]
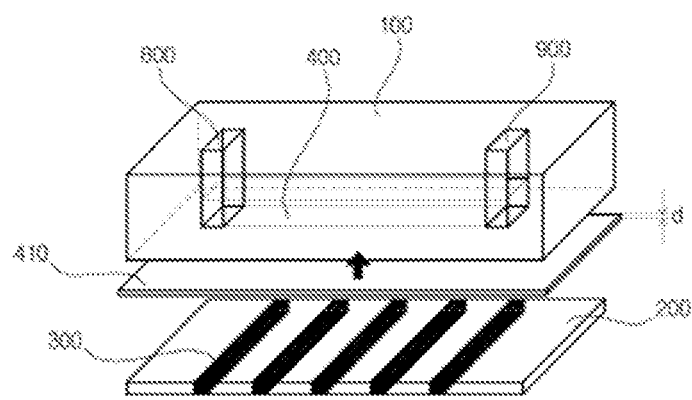
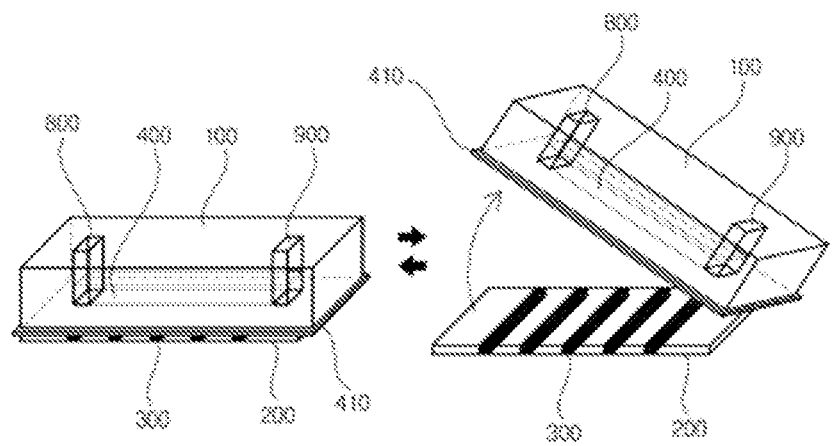

[FIG. 2]
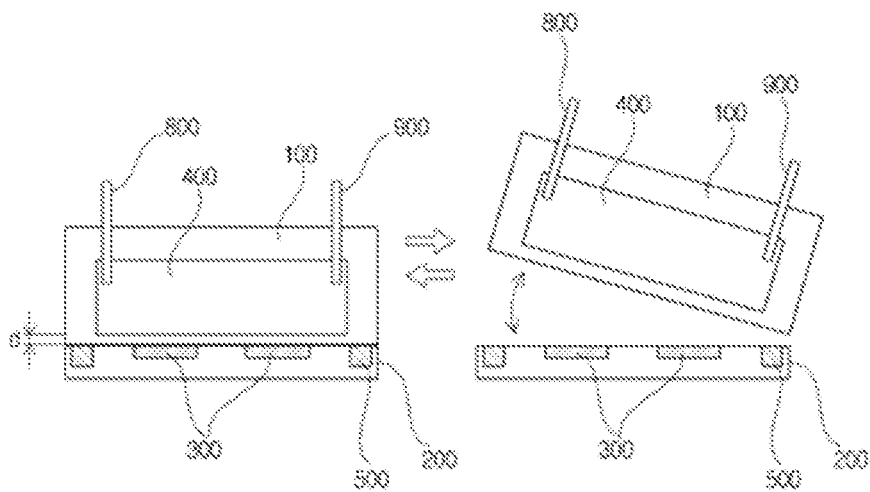

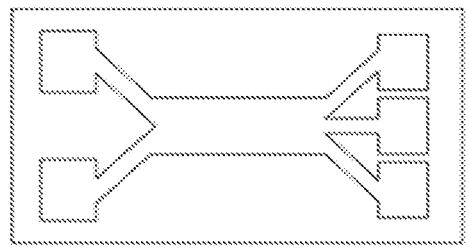
[FIG. 3]

[FIG. 4]
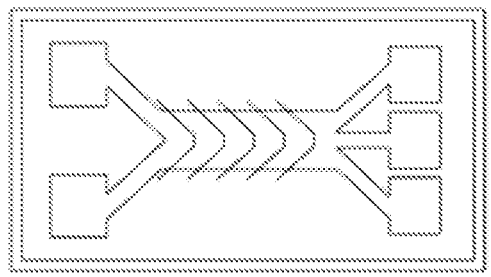

[FIG. 5]
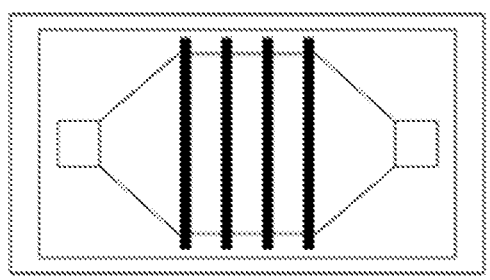

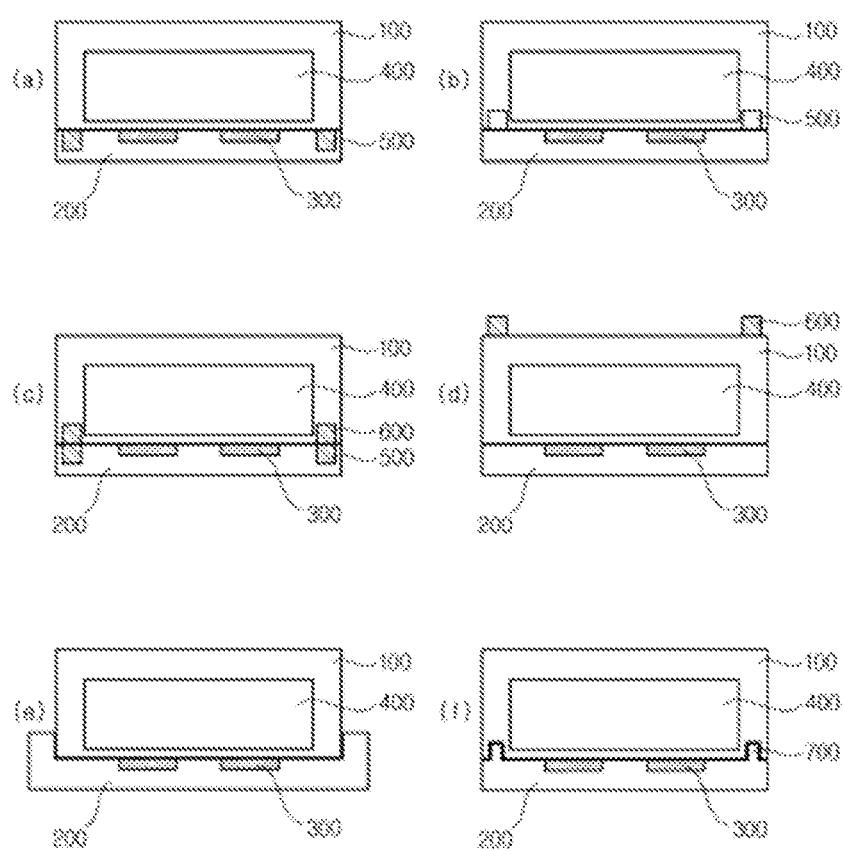
[FIG. 6]

[FIG. 7]
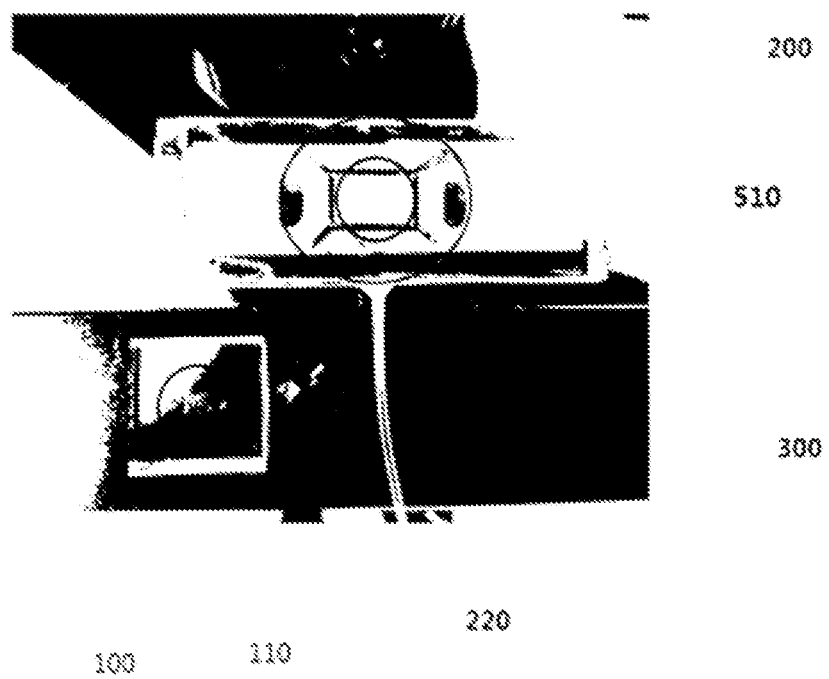

[FIG. 8]
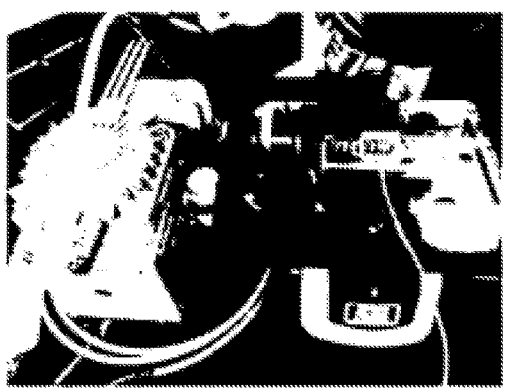
Vacuum pump
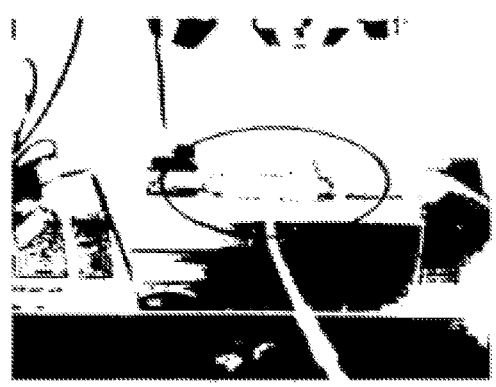
Top panel and lower panel are bonded together in vacum.

[FIG. 9]
600      600

[FIG. 10]
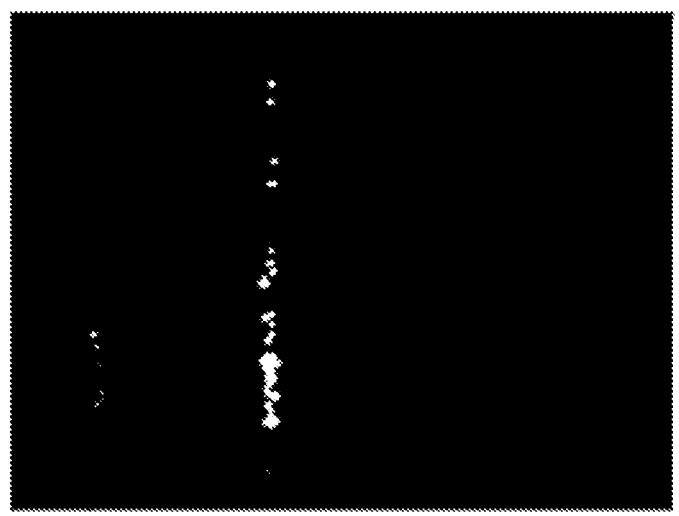

[FIG. 11]
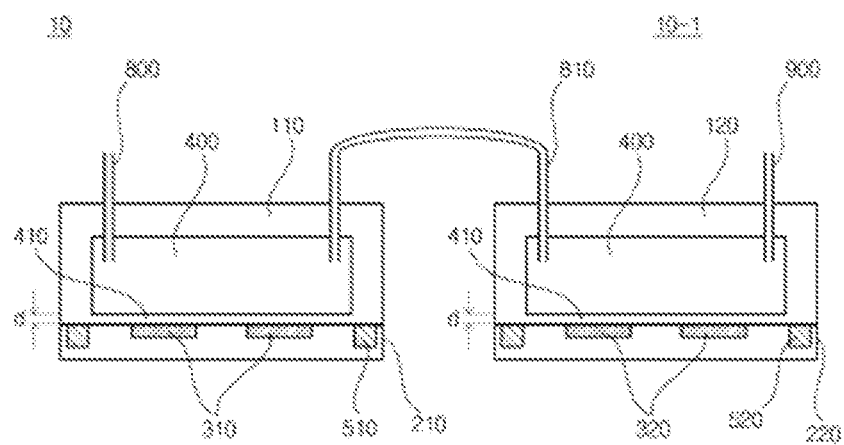

[FIG. 12]
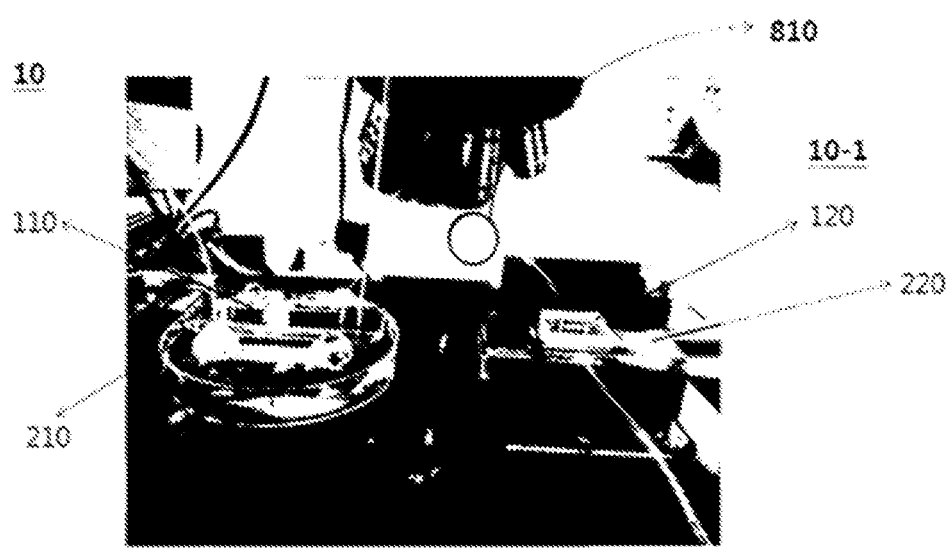

[FIG. 13]
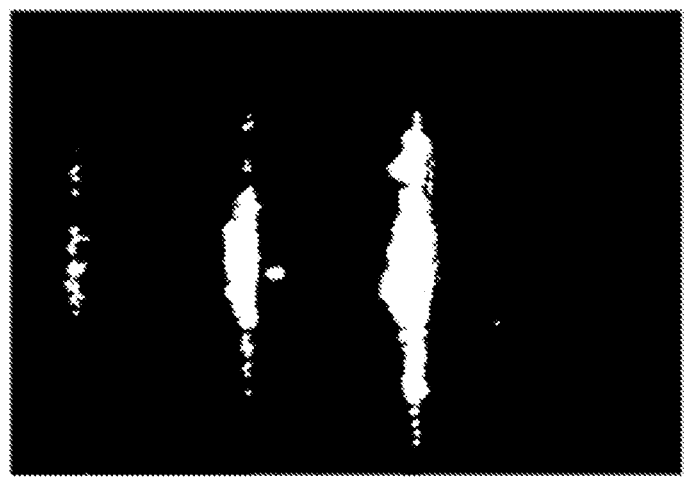

MICROPARTICLE SEPARATION APPARATUS ASSEMBLY COMPRISING MULTIPLE SEPARABLE PANELS

CROSS-REFERENCE TO RELATED APPLICATIONS

This application is a 371 of PCT/KR2015/004938, filed on May 18, 2015, which claims the benefit of Korean Patent Application No. 10-2015-0049370 filed Apr. 8, 2015, the contents of each of which are incorporated herein by reference.

BACKGROUND OF THE INVENTION

Field of the Invention

The present invention relates to a microparticle separation apparatus assembly comprising multiple separable panels, more specifically, to a microparticle separation apparatus assembly having a novel structure, comprising: a first panel comprising a magnetic microstructure for applying magnetophoretic force to microparticles to be separated; and a second panel through which a sample comprising microparticles passes, the first and second panels being made separable from each other, wherein the first panel comprising the magnetic microstructure can be recycled multiple times.

Discussion of the Related Art

With the recent development of microprocessing technology, active research is being done to manufacture microelectronic devices for concentrating, assembling, and separating microparticles and applying them in the fields of biology, chemistry, and new materials.

In such microelectronic devices, various electrokinetic principles such as electrophoresis, dielectrophoresis, and electro-osmosis may be commonly used to precisely drive or separate microparticles, proteins, cells, bacteria, etc.

Magnetophoresis separation technology using high gradient magnetic separation (HGMS) has been steadily studied for a long time because of its simple structure, high efficiency, ease of use, and because it has no hydrolysis characteristic compared to dielectrophoresis.

Conventional magnetophoresis works by employing a magnetic energy source, which is for applying a magnetic field for the magnetophoresis of a magnetic sample to be separated, and a magnetic microstructure domain, which is for amplifying the gradient in the magnetic field applied by the external magnetic energy source, in which the magnetic field from the magnetic energy source is applied to the magnetic sample to separate it according to the gradient in the magnetic density In an example, Korean Patent Registration No. 10-0791036 discloses a method for separating desired particles by arranging a ferromagnetic structure next to a microfluidic channel and applying an external magnetic field in a direction perpendicular to the flow of the sample. In the existing apparatus for separating and capturing microparticles, a bottom panel comprising a magnetic microstructure and a channel through which a sample comprising microparticles moves are integrated together. Thus, the bottom panel comprising a magnetic microstructure for applying magnetophoretic force to the microparticles is not contaminated with the sample but cannot be reused after it is used once. As a result, the bottom panel and the top panel should be entirely manufactured again, thus leading to a cost increase in the manufacture of microparticle separation apparatus.

SUMMARY OF THE INVENTION

An aspect of the present invention is directed to providing a microparticle separation apparatus having a novel structure, comprising: a first panel comprising a magnetic microstructure for applying magnetophoretic force to microparticles; and a second panel through which a sample comprising microparticles passes, the first and second panels being made separable from each other, wherein the first panel comprising the magnetic microstructure and adjusting the path of microparticles to be separated can be repeatedly used.

An exemplary embodiment of the present invention provides a microparticle separation apparatus assembly comprising: a first panel comprising a magnetic microstructure; and a second panel, which can be separated from the first panel and through which a sample passes.

FIGS. 1 and 2 show a cross-sectional view and exploded view of a microparticle separation apparatus according to the present invention.

As shown in FIG. 1, the microparticle separation apparatus according to the present invention comprises a first panel (200) comprising a magnetic microstructure, a second panel (100), which is separated from the first panel, comprising a microstructure through which a sample passes, and a thin film portion (410) formed at a part where the first panel (100) and the second panel (200) adjoin.

In the microparticice separation apparatus assembly according to the present invention, the magnetic microstructure included in the first panel is not specifically limited as long as it is a material that can form a magnetic field.

In the microparticle separation apparatus according to the present invention, the magnetic microstructure included in the first panel forms a pattern that slopes at a predetermined angle with respect to the direction of cell flow in the second panel, in order to adjust the direction of a magnetic field generated to separate the micro particles.

In the microparticle separation apparatus according to the present invention, the magnetic microstructure included in the first panel comprises a pattern that is formed in a direction perpendicular to the direction in which a sample enters and flows through a microchannel formed in the second panel.

As shown in FIGS. 1 and 2, the second panel (100) according to the present invention may further comprise an injection port (800) for injecting a sample comprising microparticles into the microchannel and an outlet port (900) for letting out separated microparticles from the microchannel.

As shown in FIGS. 1 and 2, in the second panel of the microparticle separation apparatus according to the present invention, the part where the first panel and the second panel adjoin is formed by a thin film portion (410) that is 50 μm thick or less.

That is, the microparticle separation apparatus according to the present invention is characterized in that the first panel (200) and the second panel (100) are made separable from each other, and a thin film portion (410) that is 50 μm thick or less is formed between the second panel and the first panel so that a magnetophoretic force induced by the magnetic microstructure in the first panel is transferred to a sample passing through the second panel.

In the microparticle separation apparatus according to the present invention, the thin film portion (410) may be made separable from the second panel, as shown in FIG. 1, or may be formed integrally with the second panel, as shown in FIG. 2.

In the microparticle separation apparatus according to the present invention, materials for forming the above thin film portion are not specifically limited and may include plastic materials such as PET, PI, PE, PP, and PMMA or glass.

FIG. 3 schematically shows a second panel comprising a microchannel through which a sample passes through, in the microparticle separation apparatus according to the present invention. FIGS. 4 and 5 show structures according to various exemplary embodiments of a magnetic microstructure in the parts from which the sample of FIG. 3 is separated and captured.

In the microparticle separation apparatus according to the present invention, a coupling portion for coupling the first panel and the second panel is included between the first panel and the second panel.

In the microparticle separation apparatus according to the present invention, the coupling portion is not specifically limited, and comprises a vacuum application part or a magnet. In the microparticle separation apparatus according to the present invention, the coupling portion comprises an uneven portion that is coupled to the first panel and the second panel in a corresponding manner.

FIG. 6 shows various examples of the coupling portion in the microparticle separation apparatus according to the present invention. The coupling portion may be a vacuum application part (500), as shown in (a), (b), and (c) of FIG. 6, or may be a magnet (600), as shown in (d) of FIG. 6. As shown in (a), (b), and (c) of FIG. 6, the vacuum application part (500) may be formed on either the first panel or the second panel or on both the first panel and the second panel.

Moreover, as shown in (e) and (f) of FIG. 6, the coupling portion may comprise a receiving portion that is formed by recessing the center of the first panel to receive the second panel or an uneven portion (700) that is coupled to the first panel and the second panel in a corresponding manner, or other types of coupling portions that a person skilled in the art may select to fix the first panel and the second panel.

In the microparticle separation apparatus according to the present invention, a plurality of first or second panels separated from one another may be connected. That is, as shown in FIG. 11, the microparticle separation apparatus according to the present invention is characterized in that the first panel is formed by horizontally connecting a (1-1)th panel, a (1-2)th panel, . . . , a (1-n)th panel (n is an integer greater than or equal to 1), which are separated from one another. The microparticle separation apparatus according to the present invention is characterized in that a (2-1)th panel, a (2-2)th panel, . . . , a (2-n)th panel, which are separated from one another, may be consecutively connected in a horizontal direction. A means for connecting between the horizontally connected first panels is not specifically limited, and an injection port for injecting a sample comprising microparticles into the microchannel may be connected to a connecting portion (810).

The microparticle separation apparatus according to the present invention is characterized in that the (1-n)th panel is connected to the (2-n)th panel in a vertical direction. The microparticle separation apparatus according to the present invention is characterized in that the (1-n)th panel adjoins the (2-n)th panel in the thin film portion. In the microparticle separation apparatus according to the present invention, the first panel may be positioned on top of the second panel, or the second panel may be positioned on top of the first panel.

In the microparticle separation apparatus according to the present invention, the pattern included in the magnetic microstructure may differ between the plurality of panels connected to one another, and a portion for separating cells and a portion for capturing cells may be formed into different shapes.

As shown in FIG. 4, in the microparticle separation apparatus according to the present invention, the magnetic microstructure included in the first panel comprises a pattern that is formed in a direction perpendicular to the direction in which a sample enters.

In the microparticle separation apparatus according to the present invention, the magnetic microstructure included in the (1-n)th panel is perpendicular to the flow of the sample.

Preferably, since cells do not flow anymore but are captured due to a plurality of magnetic patterns formed perpendicular to the direction in which the sample flows, a panel comprising a pattern formed perpendicular to the direction in which the sample enters may be the last one that is formed.

In the microparticle separation apparatus according to the present invention, the first panel comprising a reusable magnetic microstructure and the second panel made for one time use through which the sample passes may further comprise an alignment part for aligning the magnetic microstructure and a fluidic channel through which the sample passes. The form of the alignment part is not specifically limited.

The microparticle separation apparatus according to the present invention is economically efficient, since a first panel comprising a magnetic microstructure is separated from a second panel comprising a microstructure through which a sample passes and therefore the second panel through which the sample passes can be used only once depending on the sample while the first panel comprising the magnetic microstructure can be repeatedly used multiple times.

BRIEF DESCRIPTION OF THE DRAWINGS

FIGS. 1 and 2 show a microparticle separation apparatus assembly according to the present invention;

FIGS. 3 to 5 show magnetic microstructure patterns of first and second panels in a microparticle separation apparatus assembly according to an exemplary embodiment of the present invention;

FIG. 6 shows various exemplary embodiment of a coupling portion in the microparticle separation apparatus according to the present invention;

FIGS. 7 to 9 show the microparticle separation apparatus manufactured according to the exemplary embodiment of the present invention;

FIG. 10 shows cells separated by using the microparticle separation apparatus manufactured according to the exemplary embodiment of the present invention;

FIGS. 11 and 12 show a microparticle separation apparatus manufactured according to another exemplary embodiment of the present invention; and FIG. 13 shows cells separated by using the microparticle separation apparatus manufactured according to an exemplary embodiment of the present invention.

DETAILED DESCRIPTION OF THE ILLUSTRATED EMBODIMENTS

Hereinafter, exemplary embodiments of the present invention will be described in further details. However, the present invention is not limited to the following embodiments.

Manufacturing Example 1

FIG. 7 shows a first panel and a second panel that are made separable from each other. FIG. 8 shows the first and second panels that are made separable from each other that are connected to a vacuum pump and bonded together by applying vacuum. FIG. 9 shows the first and second panels that are bonded to the thin film portion by placing a magnet over the second panel.

As shown in FIG. 7, the first panel (200) comprises a magnetic microstructure (300) and a vacuum application part (510) for applying vacuum near the magnetic microstructure. The second panel (100) comprises a microchannel structure (110) that is separated from the first panel and can be separated and captured as a sample passes through it.

As shown in FIG. 9, the first and second panels made separable from each other are bonded to the thin film portion by putting them over a ferromagnet and placing a magnet (600) over the second panel.

Test Example 1

FIG. 10 shows a fluoroscopic image of cells that are separated and captured on a capturing portion by using the microparticle separation apparatus assembly made separable according to the present invention that is manufactured in the manufacturing example 1.

Manufacturing Example 2

As shown in the schematic diagram of FIG. 11, a microparticle separation apparatus assembly was manufactured by connecting a plurality of separated panels.

A (1-1)th panel (210) comprising a magnetic microstructure (310) for separating a sample and a (1-2)th panel (220) separated from the (1-1)th panel and comprising a magnetic microstructure (320) for capturing a sample, which is formed in a direction perpendicular to the direction in which a sample enters, were manufactured.

Moreover, a (2-1)th panel (110) connected to the (1-1)th panel (210) and comprising a channel for separating a sample and a (2-2)th panel (120) connected to the (1-2)th panel and comprising a chamber for capturing cells within a separated sample were manufactured.

After the manufacture of a thin-film portion, a firstassembly (10) in which the (1-1)th panel and the (2-1)th panel adjoin with the thin film portion in between and a second assembly (10-1) formed by connecting the (1-2)th panel and the (2-2)th panel are laminated, and then the first assembly (10) and the second assembly (10-1) are connected by a connecting portion (810) so that a sample separated on the (2-1)th panel is captured on the (2-2)th panel. The connection state is depicted in FIG. 12.

FIG. 13 shows a fluoroscopic image of cells that are separated and captured on a capturing portion by using the microparticle separation apparatus assembly that is manufactured in the above manufacturing example.

What is claimed is:

1. A microparticle separation apparatus assembly comprising:
   a first panel comprising a magnetic microstructure;
   a second panel detachable from the first panel and including a microchannel structure through which the sample passes; and
   a thin film portion between the second panel and the first panel, the thin film portion having a thickness of 50 um or less and made of PET, PI, PE, PP, PMMA or glass,
   wherein the magnetic microstructures included in the first panel include a pattern formed in a direction perpendicular to the direction in which the sample is introduced.

2. The microparticle separation device assembly according to claim 1, wherein the magnetic microstructures included in the first panel are inclined at an angle with respect to a flow direction of cells in the second panel.

3. The microparticle separation device assembly of claim 1, further comprising a coupling portion for coupling the first panel and the second panel.

4. The microparticle separation device assembly of claim 3, wherein the coupling portion comprises a vacuum applying portion, or a magnet.

5. The fine particle separator assembly of claim 3, wherein the coupling portion includes concave and convex portions formed in correspondence with the first panel and the second panel.

6. The apparatus of claim 1, wherein the first panel comprises n first 1-1 panels, a 1-2 panel, and a first-n panel are connected.

7. The apparatus of claim 1, wherein the second panel comprises n second-1 panels, second-2 panels, and a second-n panel are connected.

8. The fine particle separation apparatus according to claim 6, wherein the first-n panel is in contact with the second-n panel and the thin film part.

9. The microparticle separation device assembly of claim 8, wherein the magnetic microstructures included in the first-n panel are perpendicular to the sample flow direction.

10. The microparticle separation device assembly of claim 1, wherein the first panel is located on top of the second panel.

11. The microparticle separation device assembly of claim 1, wherein the first panel is located below the second panel.

12. The microparticle separation device assembly of claim 1, wherein the first panel and the second panel further comprise an alignment portion for aligning the sample fluid channel with the magnetic microstructure.

13. The fine particle separation apparatus according to claim 7, wherein the first-n panel is in contact with the second-n panel and the thin film part.

* * * * *